United States Patent [19]
Kobayashi et al.

[11] Patent Number: 6,064,484
[45] Date of Patent: May 16, 2000

[54] PATTERN INSPECTION METHOD AND SYSTEM

[75] Inventors: Ken-ichi Kobayashi; Takayoshi Matsuyama; Showgo Matsui, all of Kawasaki, Japan

[73] Assignee: Fujitsu Limited, Kawasaki, Japan

[21] Appl. No.: 08/814,414

[22] Filed: Mar. 11, 1997

[30] Foreign Application Priority Data

Mar. 13, 1996 [JP] Japan ................................. 8-056474

[51] Int. Cl.$^7$ ................................................. G01B 11/00
[52] U.S. Cl. ........................... 356/390; 356/384; 356/237
[58] Field of Search .................................... 356/390, 372, 356/375, 384, 237

[56] References Cited

U.S. PATENT DOCUMENTS 4,448,532  5/1984  Joseph et al. .
4,926,489  5/1990  Danielson et al. .
5,369,430  11/1994  Kitamura ............................. 348/94

FOREIGN PATENT DOCUMENTS 3-51747  3/1991  Japan .

*Primary Examiner*—Frank G. Font
*Assistant Examiner*—Reginald A. Ratliff
*Attorney, Agent, or Firm*—Staas & Halsey

[57] ABSTRACT

A pattern inspection method includes the steps of: obtaining first image data by optically picking up an actually formed pattern such as a reticle; aligning a position of the first image data with second image data of a pattern at a different layer from that of the first image data; and performing a first pattern inspection using the first and second image data. Defect inspection can be executed in a short time with a practically sufficient precision.

28 Claims, 13 Drawing Sheets

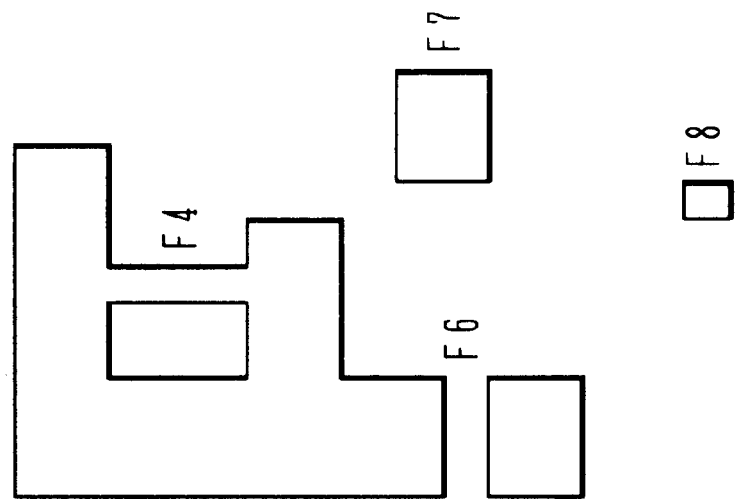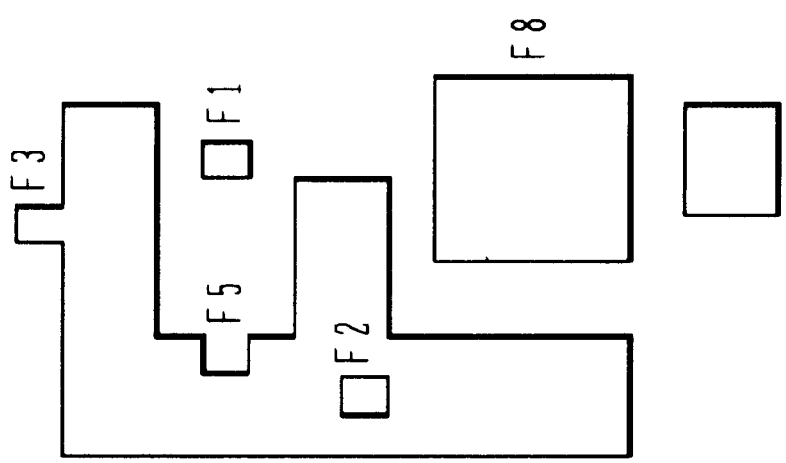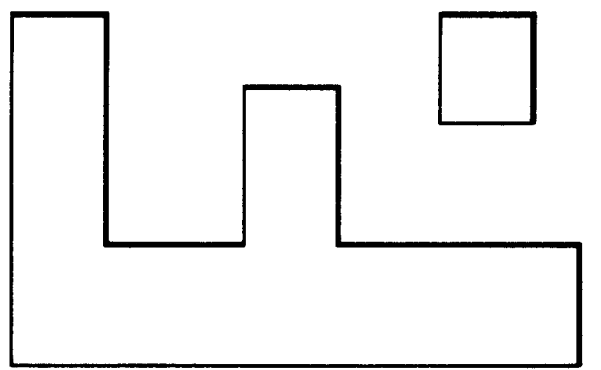

n x 90°
ROTATION
INCLUSIVE

FIG.10H
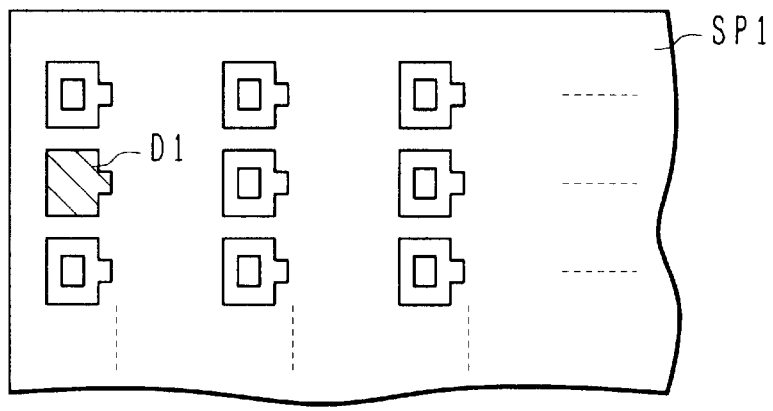
FIG.10I                    FIG.10J
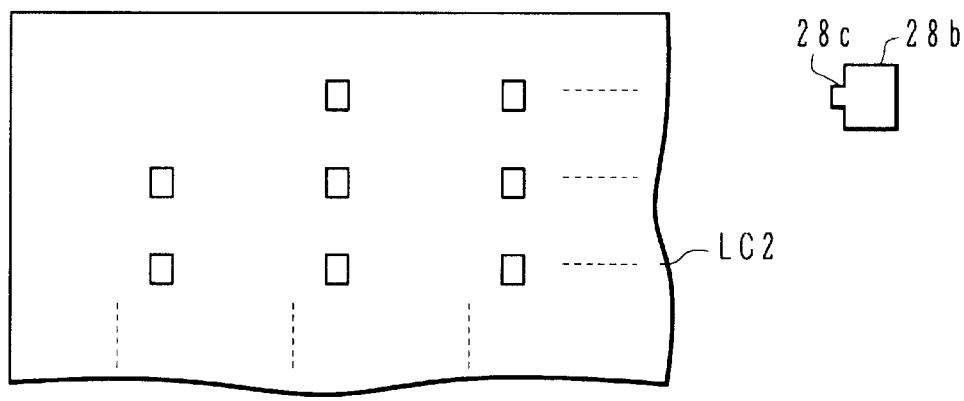
FIG.10K
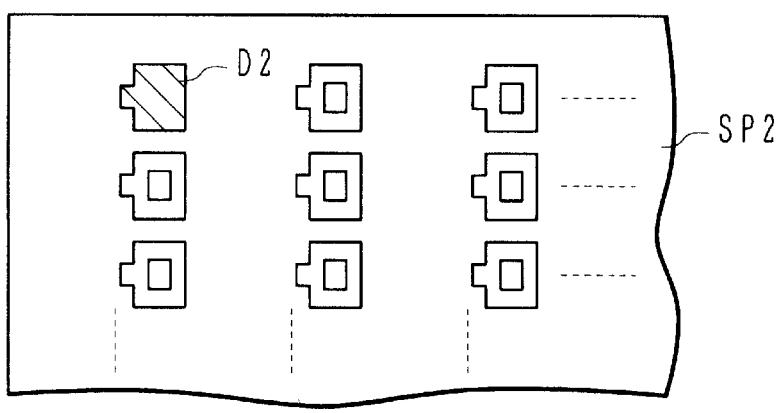

FIG.11A FIG.11B
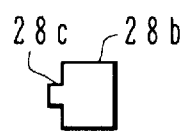
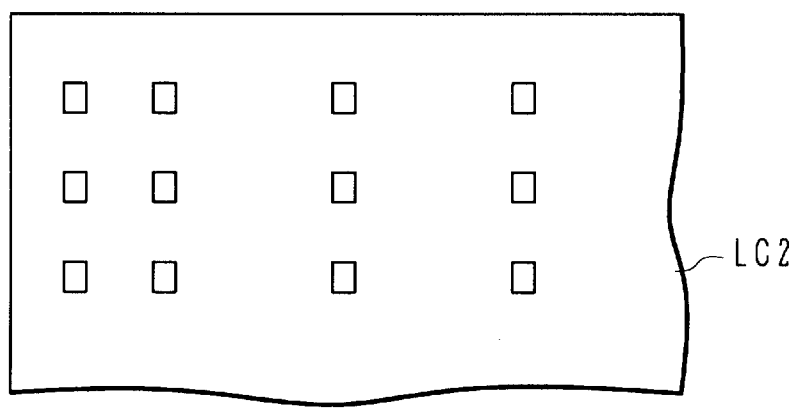
FIG.11C
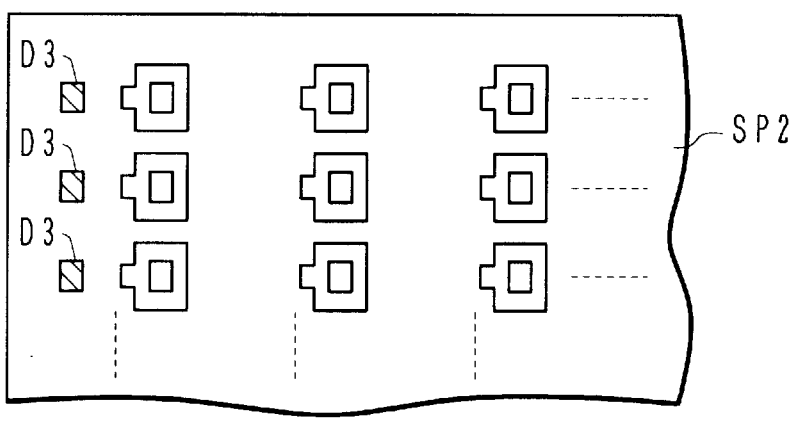

PATTERN INSPECTION METHOD AND SYSTEM

This application is based on Japanese patent applications 8-56474 and 9-51957, filed on Mar. 13, 1996 and Mar. 6, 1997, all the contents of which are incorporated herein by reference.

BACKGROUND OF THE INVENTION a) Field of the Invention

The present invention relates to pattern defect inspection, and more particularly to inspection of a defect of a pattern formed on reticles, photomasks, or wafers, or of a database representing a pattern.

b) Description of the Related Art

Various patterns are formed on semiconductor wafers during manufacture of semiconductor devices. Generally, a reticle or mask having a pattern of an original layout is optically transferred in a reduced size or in the same 1:1 size to a resist layer coated on a semiconductor wafer, and developed to form a resist mask. By using this resist mask as a process mask, the underlying layer is processed.

A plurality of photolithography processes are generally carried out for the completion of a single semiconductor device. A mask is used at each of these photolithography processes. The number of masks used is called a mask layer number.

As semiconductor devices are becoming of high density and high integration, the amount of pattern data has increased and the inspection time of patterns has increased. Even fine defects may affect circuit performance because patterns are becoming very narrow. It is therefore desired to detect even a fine pattern defect without fail.

A fine pattern actually formed by using a designed pattern becomes different from the designed pattern because of interferences of light in lithography process or the like during manufacture. For example, although corners of a pattern have right angle apexes when designed, the actual corners formed are rounded. The design data does not therefore coincide with the actual pattern with respect to corners.

If an actually formed pattern is inspected at high sensitivity by using a designed pattern as reference at high sensitivity, all corners are judged as defects. However, these corners are not real defects but are within allowance. Such defects will be called quasi defects. Since quasi defects are permitted to exist, these defects are desired not to be detected by defect inspection. In order not to detect such quasi defects by inspection, a rounding process or the like becomes necessary for corners of the design data.

Various types of processes including the rounding process are therefore required in detecting detects by comparison between a formed pattern and data in a database, so that it takes a long time to carry out defect inspection.

In the manufacture of semiconductor integrated circuits, a number of semiconductor chips having same patterns are usually formed on a single semiconductor wafer. These semiconductor chips (dies) are sequentially exposed with a stepper by using the same reticle pattern so that each die has the same pattern. By comparing the dies having the same pattern, an abnormal pattern accidentally formed on a particular die can be detected reliably. This comparison inspection of dies can be performed at relatively high speed and can provide a high defect detection sensitivity.

A reticle to be used for the exposure of semiconductor chips has in some cases a plurality of same patterns, for example, 2×2 patterns. In this case, comparison inspection of a plurality of areas of the reticle having the same patterns can also be performed similar to the comparison inspection of dies with the same pattern.

If a plurality of reticles, even if each reticle has a single same pattern, are formed, the comparison inspection of reticles can be performed at high defect detection sensitivity. This inspection is generally called a plate-to-plate inspection.

Such a die-to-die comparison inspection or plate-to-plate comparison inspection will be called hereinafter a same pattern comparison inspection.

The same pattern comparison inspection can be performed at high speed and at high defect detection sensitivity. However, for example, if a designed pattern itself has a defect or if dust is attached to the reticle during exposure and the same pattern with the dust defect is exposed to a number of dies, such defects cannot be detected by the same pattern comparison inspection.

In such a case, a defect inspection process described above is necessary, which process detects a defect by comparison of an actual pattern and design data in a database. However, comparison between different kind of patterns, such as data in a database and a pattern on a reticle, may result in a quasi defect described above if it is performed at high defect detection sensitivity, and a long time is required for a defect inspection work.

Techniques of comparison inspection of a die and database has been proposed, for example, in JP-A-3-51747 in which three object optical systems are provided, comparison inspection of dies is performed based on image data taken by the two object optical systems, and the comparison inspection of a die and database is performed through comparison between image data taken by the other object optical system and the image data obtained from a database. Although the die-to-die comparison inspection and the die-to-database comparison inspection can be performed concurrently, the comparison inspection process takes a long time because the image data in the database is different in representation from the image data of the die.

With an increase in integration density of a semiconductor integrated circuit device, the patterns thereof become complicated. There may occur such mistakes in the stage of designing the patterns that patterns which should be formed are omitted, and that patterns which should not be formed are formed. In such cases, the database itself includes mistakes.

When masks or semiconductor wafers faithful to such a database are formed, however, those mistakes cannot be detected by usual defect or fault inspection. A long time inspection becomes necessary to detect and correct such mistakes. Design processes for avoiding such design mistakes have been proposed therefore.

For example, in designing contact holes for connecting a pair of wirings, it is proposed to detect contact portions which have widened width in a wiring pattern, and to generate a contact hole pattern automatically in each contact portion.

In the case of automatically generating patterns in this way, however, patterns may be forcedly generated at positions where the patterns should not be formed. For example, when one wiring pattern is connected at one end to an underlying layer and at the other end to an upper layer, in designing contact holes for the underlying layer, a contact hole may be formed at a position where a contact hole for the upper layer should be formed.

From the viewpoint of the operation of a semiconductor device, the important point is not necessarily an absolute precision of each pattern. Rather, alignment of patterns between a plurality of layers often becomes more important than the absolute precision. For example, more important is correct alignment between a contact hole and a higher level wiring pattern, or electrical isolation between different wiring patterns.

Conventionally, each pattern has been formed to have a precision as high as possible and then is inspected to thereby ensure alignment between different layers.

Also, the reliability of database has been improved by inspecting the database itself and correcting the detected defects.

SUMMARY OF THE INVENTION

It is an object of the present invention to provide a defect inspection method capable of inspecting a defect of a pattern in a short time and providing a practically sufficient precision.

It is another object of the present invention to provide a defect inspection apparatus capable of performing such an inspection detection method.

According to one aspect of the present invention, a pattern inspection method is provided which comprises the steps of: obtaining first image data by optically picking up a pattern actually formed; aligning a position of the first image data with second image data of a pattern at a different layer from the pattern of the first image data; and performing a first pattern inspection using the first and second image data.

With a comparison inspection between the first image data and the second image data in different layer relationship with the first image data, a defect inspection with respect to interlayer alignment or registry which is very important in practice, can be performed.

The second image data may be image data of an actually formed pattern or image data generated from a database.

According to another aspect of the present invention, a pattern inspection apparatus is provided which comprises: an optical system for focussing an image of a workpiece having a first pattern on an image pickup surface; pickup means disposed on the image pickup surface of the optical system for supplying image data of the first pattern; image data supplying means for supplying image data of a second pattern at a layer different from the first pattern; and a defect detector circuit for comparing the image data of the first pattern supplied from the pickup means with the image data of the second pattern supplied from the image data supplying means.

According to further aspect of the present invention, there is provided a pattern inspection method comprising the steps of: providing first image data on one layer; registering a first pattern which is a part of said first image data; and detecting patterns of equivalent configuration to said first pattern from said first image data, as a first group of patterns.

By extracting patterns of a specific configuration from image data, inspection of the image data, etc. is made easy.

It is preferable to further comprise the steps of providing a first associated group of patterns which are second image data on a different layer from that of said first image data; and comparing said first group of patterns and said first associated group of patterns.

It is also preferable to further comprise the steps of providing second associated group of patterns which are third image data on a different layer than said first group of patterns and said first associated group of patterns; registering a second pattern which is another part of said first image data than said first pattern; detecting patterns of equivalent configuration to said second pattern from said first image data, as second group of patterns; comparing said second group of patterns and said second associated group of patterns.

According to yet a further aspect of this invention, there is provided a pattern inspection system comprising: means for providing first image data on one layer; register connected to said means and capable of registering a first pattern which is a part of said first image data; and a detector connected to said means and said register, and capable of detecting patterns of equivalent configuration to said first pattern from said first image data, as a first group of patterns.

As above, patterns can be inspected at high sensitivity and with high reliability in a short time.

BRIEF DESCRIPTION OF THE DRAWINGS

FIGS. 6A to 6C are schematic plan views showing examples of types of patterns and detects.

FIGS. 10A to 10K are a schematic cross section of a semiconductor device and schematic plan views of patterns for illustrating another example of defect detection.

FIGS. 11A to 11C are schematic plan views of patterns for illustrating another example of defect detection.

DETAILED DESCRIPTION OF THE PREFERRED EMBODIMENTS

Figure 1:
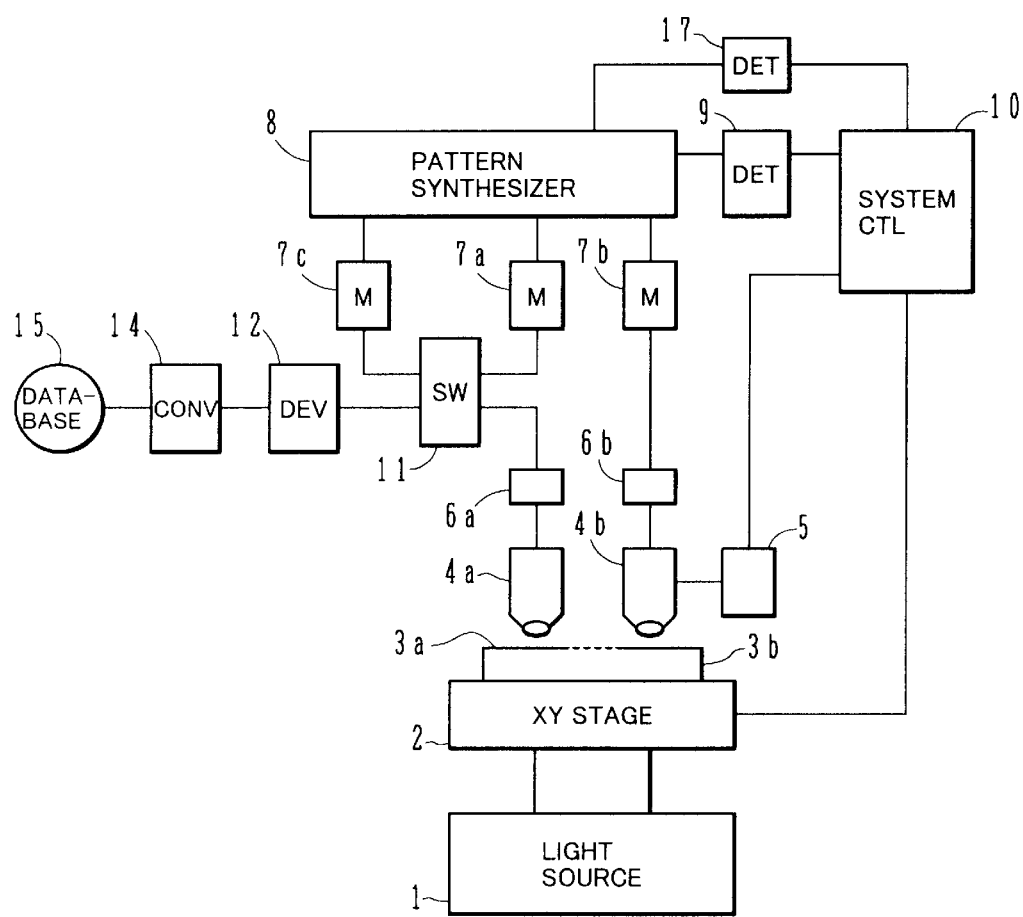
FIG. 1 is a block diagram showing the structure of a pattern inspection apparatus according to an embodiment of the invention.

FIG. 1 is a block diagram showing the structure of a defect inspection apparatus according to an embodiment of the invention. Illumination light from a light source 1 is applied to an inspection workpiece 3 (3a, 3b) placed on an XY stage. The inspection workpiece 3a, 3b may be a semiconductor wafer having a plurality of inspection areas or a pair of masks (including reticles) having the same pattern. The inspection workpiece may also be a glass substrate of a liquid crystal display. It may be any fine pattern formed on or in a substrate and requiring inspection.

A pair of object optical systems 4a and 4b are disposed above the inspection workpiece 3a, 3b. A pair of light reception elements 6a and 6b are placed on the image surfaces of the object optical systems 4a, 4b. The light reception elements 6a, 6b may be line sensors made of CCDs. The focus of the object optical systems 4a, 4b are adjusted by an automatic focussing mechanism 5. The inspection workpiece 3a, 3b can be two-dimensionally scanned by moving the XY stage 2. An image in an inspection area is picked up by the light reception elements 6a, 6b.

Image data generated by the light reception elements 6a, 6b are sent to image memories 7a, 7b. The light reception element 6b is always connected to the image memory 7b, whereas the light reception element 6a is selectively connected to the image memory 7a via a selector switch 11.

Another image memory 7c is also provided to which image data from a database is selectively supplied via the selector switch 11. In the structure shown in FIG. 1, design data or exposure data 15 is supplied to an image developer 12 via a data converter 14, and then to the image memory 7c via the selector switch 11.

The image memories 7a, 7b, 7c are connected to a pattern synthesizer 8 which can synthesize a plurality of supplied images in proper alignment with their positions.

A fine defect detector 9 is a circuit which can detect a fine defect from an image obtained by synthesizing a plurality of superposed images. For example, image data supplied from the image memories 7a and 7b are compared to detect a minute difference between the image data and supply fine defect information.

Another defect detector 17 detects a defect of the synthesized image in accordance with a design rule. The fine defect detector 9 and defect detector 17 are controlled by a system controller 10 which also controls the automatic focussing mechanism 5 and XY stage 2. The system controller is equipped with a display and a keyboard and/or control panel.

There are two important points of this structure. One point is that the selector switch 11 can connect the light reception element 6a and image developer 12 to the image memories 7a and 7c, selectively or both at the same time. The other point is that the defect detector 17 can inspect not only the identicalness but also the relationship between a plurality of image data sets. With these two functions, in addition to the die-to-die (or plate-to-plate) comparison inspection and the die-to-database (or plate-to-database) comparison inspection similar to conventional techniques, a comparison inspection of image data between different layers can also be performed. Both the die-to-die (or plate-to-plate) comparison inspection similar to conventional techniques and the comparison inspection of image data between different layers can be performed at the same time.

Figure 2:
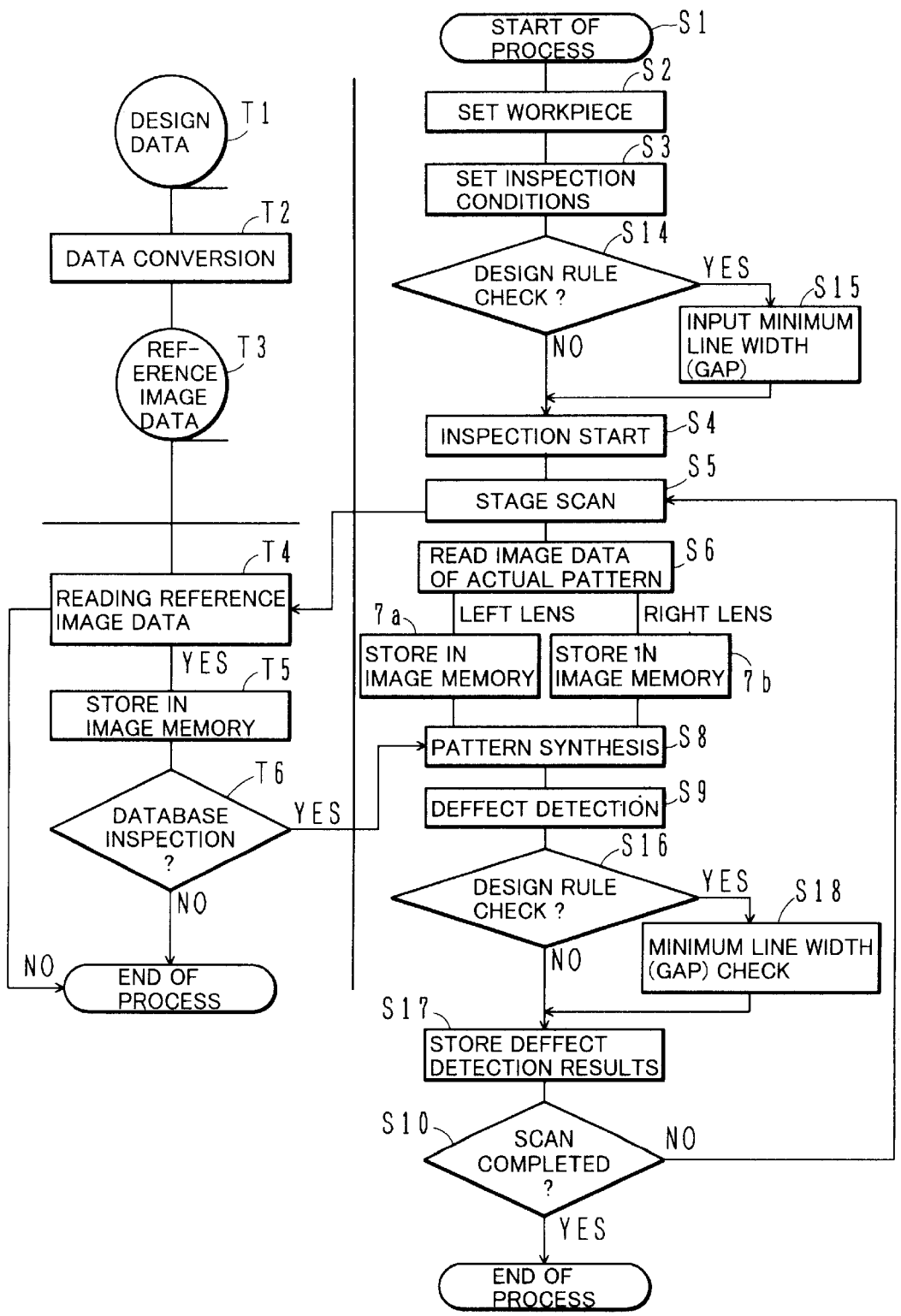
FIG. 2 is a flow chart demonstrating a pattern inspection method according to an embodiment of the invention.

FIG. 2 is a flow chart briefly demonstrating a defect inspection process to be performed by the defect inspection apparatus shown in FIG. 1.

The left side in FIG. 2 demonstrates a process at the database side to be executed by the database 15, data converter 14, and image developer 12, and the right side in FIG. 2 demonstrates a process to be performed at other portions of the inspection stage. First, at step T1, design data (or exposure data) is read. At step T2, the read data is converted to generate at step T3 reference image data to be compared with actual image data. The processes up to the process of generating and storing the reference image data are a pre-inspection work to be performed prior to reading an actual image and inspecting it.

The process on the inspection stage side at the right side in FIG. 2, starts at step S1. Next, at step S2, an inspection workpiece is set. This workpiece may be a single workpiece having a plurality of inspection areas or a plurality of workpieces each having a single inspection area.

At step S3, the inspection conditions are set. For example, the inspection conditions include an inspection area, a defect detection sensitivity, a lens pitch, a minimum line width for design rule check to be described later, and the like. After the inspection conditions are set at step S3, it is checked whether or not a design rule check is to be performed. If the design rule check is to be performed, the flow advances to step S15 following an arrow YES whereat a minimum line width (minimum line gap) is input. Thereafter, the flow advances to step S4. If the design rule check is not to be performed, the flow directly advances from step S14 to step S4 following an arrow NO. At step S4, inspection starts to pick up images with the light reception elements 6a and 6b.

At next step S5, the XY stage is scanned for conversion of a two-dimensional image into image data.

If the database is to be used for inspection reference, at the same time when the XY stage scanning starts, it is acknowledged at step T4 at the left side in FIG. 2 that a position signal is supplied and a process of reading the reference image data is executed. Namely, image data of an actual pattern formed on a specimen is read concurrently with reading the reference image data converted from the design data or exposure data.

At step S6, the image data is picked up from the actual pattern on the specimen. At steps S7a and S7b, the actual image data picked up through the right and left lenses is stored in the image memories 7a and 7b.

If the database is to be used for inspection reference, along with the steps S7a and S7b, the reference image data is stored in the image memory 7c. It is checked at next step T6 whether the database is in use for inspection reference. If in use, the flow advances to step S8 following an arrow YES to read the reference image data and supply it to the pattern synthesizer 8.

At step S8, the actual image data in the image memory 7b, and the reference image data read from the database and/or the actual image data in the image memory 7a, are synthesized. At next step S9, a die-to-die (or plate-to-plate) comparison inspection is performed. A die-to-database inspection may also be carried out at this step.

It is checked at next step S16 whether the design rule check has been designated. If not designated, the flow directly advances to step S17 following an arrow NO to register the defect detection results. If designated, the flow advances to step S18 following an arrow YES to check the design rule such as a minimum line width and a minimum line gap. Thereafter, the flow advances to step S17.

For the defect inspection using the design rule, the reference image data read from the database and the actual image data picked up with the light reception element may be compared. Alternatively, the actual image data already read may be used in place of the reference image data read from the database. In the defect inspection using the design rule, it is checked whether the pattern width is in conformity with the design rule (minimum line width check) or whether adjacent patterns have a predetermined gap (minimum line-to-line gap check). If the design rule is not satisfied, it is detected as a defect.

At step S10 it is checked whether scanning of the whole area has been completed. If not, the flow returns to step S5 following an arrow NO, whereas if completed, the process is terminated following an arrow YES.

The outline of the defect detection process has been described above. The contents of the defect detection process change with a state of the selector switch 11.

Figure 3A:
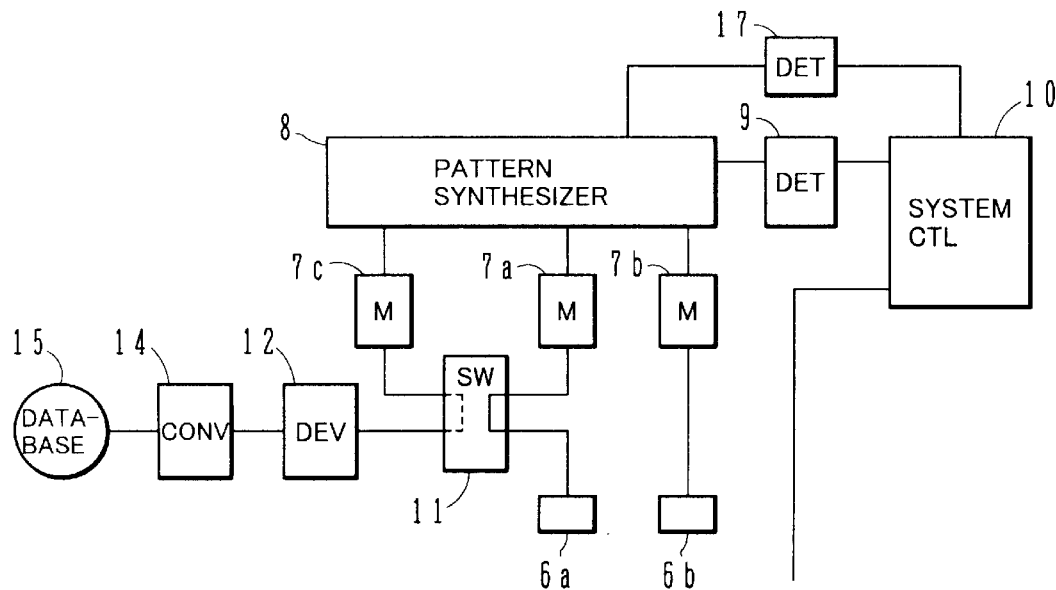
FIGS. 3A and 3B are block diagrams showing the main parts of the pattern inspection apparatus shown in FIG. 1 taking two connection states for a defect detection process.
Figure 3B:
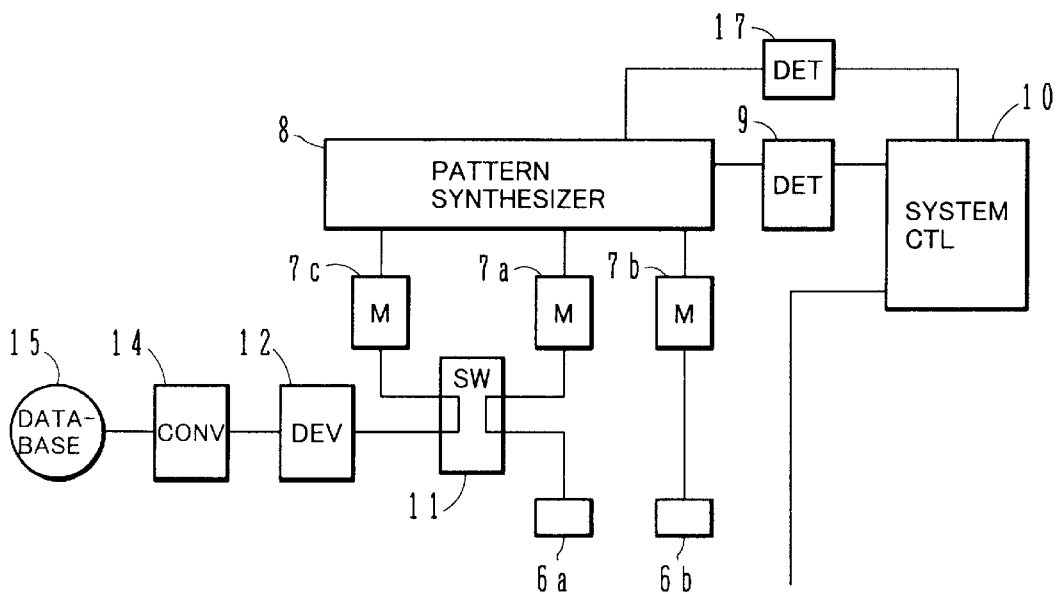

FIGS. 3A and 3B are schematic diagrams illustrating the defect detection process changing with a state of the selector switch 11.

In the connection state shown in FIG. 3A, the selector switch 11 connects either the light reception element 6a to the image memory 7a or the image developer 12 to the image memory 7c. The image data picked up with the light reception element 6b is stored in the image memory 7b for the comparison inspection with the image data in the image memory 7a or 7c. The pattern synthesizer 8 synthesizes the patterns of the image data supplied from the image memories 7a and 7b, or 7b and 7c. The fine defect detector 9 performs inspection like a conventional die-to-die (or plate-to-plate) comparison inspection. The defect detector 17 performs a comparison inspection on the gap or distance of image data at different layers and on the minimum line widths of image data having the same pattern, in accordance with the design rule or the like. As will be later described, the pattern may be divided and the gap between divided areas may also be checked.

In the connection state shown in FIG. 3B, the selector switch 11 connects both the light reception element 6a to the image memory 7a and the image developer 12 to the image memory 7c. The pattern synthesizer 8 synthesizes the patterns of the actual image data picked up with the light reception elements 6a and 6b and the reference image data supplied from the image developer 12. The fine defect detector 9 performs an inspection like a conventional die-to-die (or plate-to-plate) comparison inspection, relative to the presumably identical patterns of the actual image data supplied from the light reception elements 6a and 6b. The defect detector 17 performs a comparison inspection between the image data supplied from one of the light reception elements 6a and 6b and the reference image data supplied from the image developer 12, or a comparison inspection between image data at different layers supplied from the light reception elements 6a and 6b.

Figure 4A:
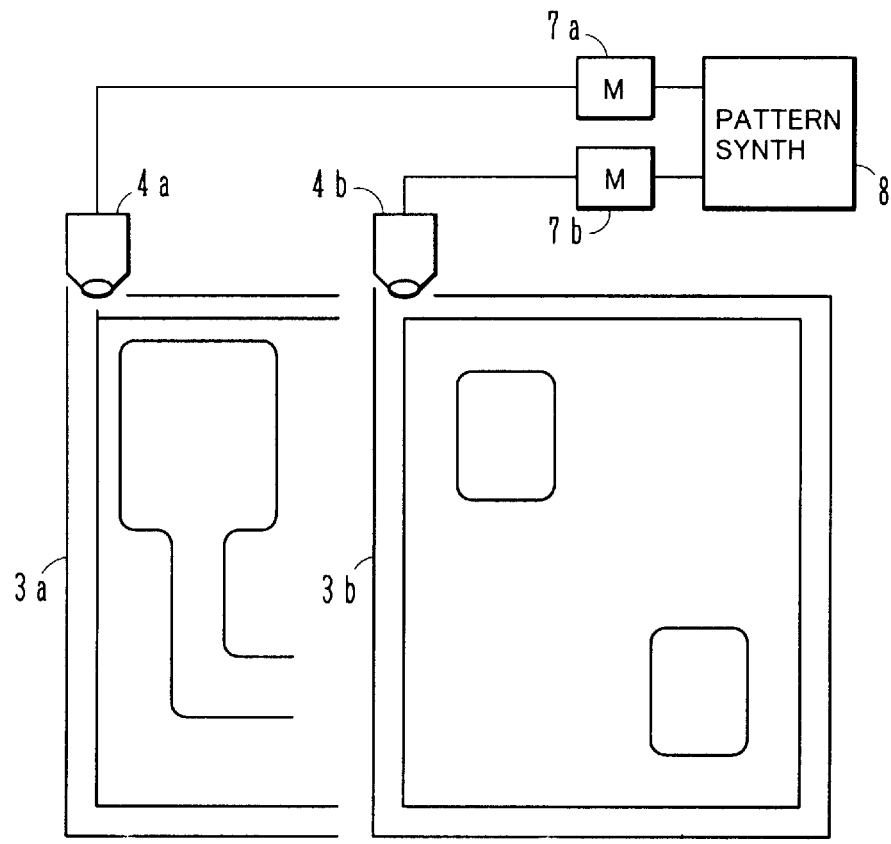
FIGS. 4A and 4B are schematic diagrams illustrating the operation of the pattern inspection apparatus taking the connection state shown in FIG. 3A.

FIG. 4A shows examples of patterns obtained at the connection state shown in FIG. 3A wherein the selector switch 11 connects the light reception element 6a to the image memory 7a. In this case, the inspection workpieces 3a and 3b have the surface patterns at different layers. For example, the inspection workpiece 3a shows a wiring pattern and the inspection workpiece 3b shows a contact hole pattern. For the inspection workpieces at different layers, the defect detector 17 performs a comparison inspection using the synthesized pattern.

Figure 4B:
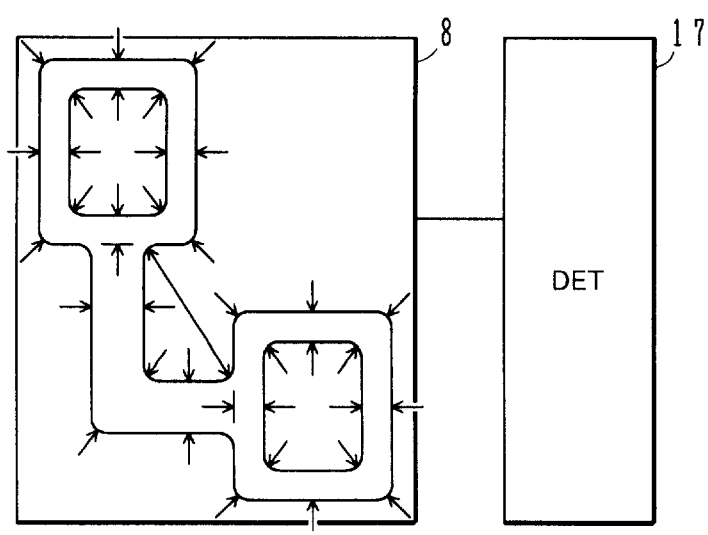

As shown in FIG. 4B, the pattern synthesizer 8 generates a synthesized pattern of the inspection workpieces 3a and 3b. The defect detector 17 divides the synthesized pattern if necessary, and checks the pattern widths of the inspection workpieces 3a and 3b, presence/absence of matching or paired lines, and distances between paired lines.

In the example shown in FIG. 4B, paired sides at a wiring pattern and a contact hole at four sides, i.e., upper, lower, right, and left sides thereof, are detected, and the distances between the paired sides are detected. The paired sides can be detected in two different layers of image data which have a strong relationship from the viewpoint of circuit function, for example by detecting two patterns having superposition, and detecting edges of the two patterns disposed in a neighborhood. Here, the term "neighborhood" is typically defined by a distance within 10 times, more typically 5 times, the minimum line width defined by a design rule. When two or more edges of one pattern are detected in response to one edge of the other pattern, the nearest one in distance may be selected.

In the figure, the paired sides are disposed in parallel. The paired sides may not necessarily be parallel. For example, paired sides may be formed of a pattern rounded edges due to interference, etc. and wider square pattern, or the like.

The defect detector 17 also measures the width of the remaining portion of a wiring pattern and checks it in accordance with the design rule. For example, if the width of the wiring pattern is so narrow that the design rule check cannot be performed, it is detected as a defect.

In the above description, patterns at different layers are picked up with the light reception elements 6a and 6b. The light reception elements 6a and 6b may pick up same repetitive patterns. In this case, instead of the defect detector 17, the fine defect detector 9 checks a difference between patterns.

Figure 5:
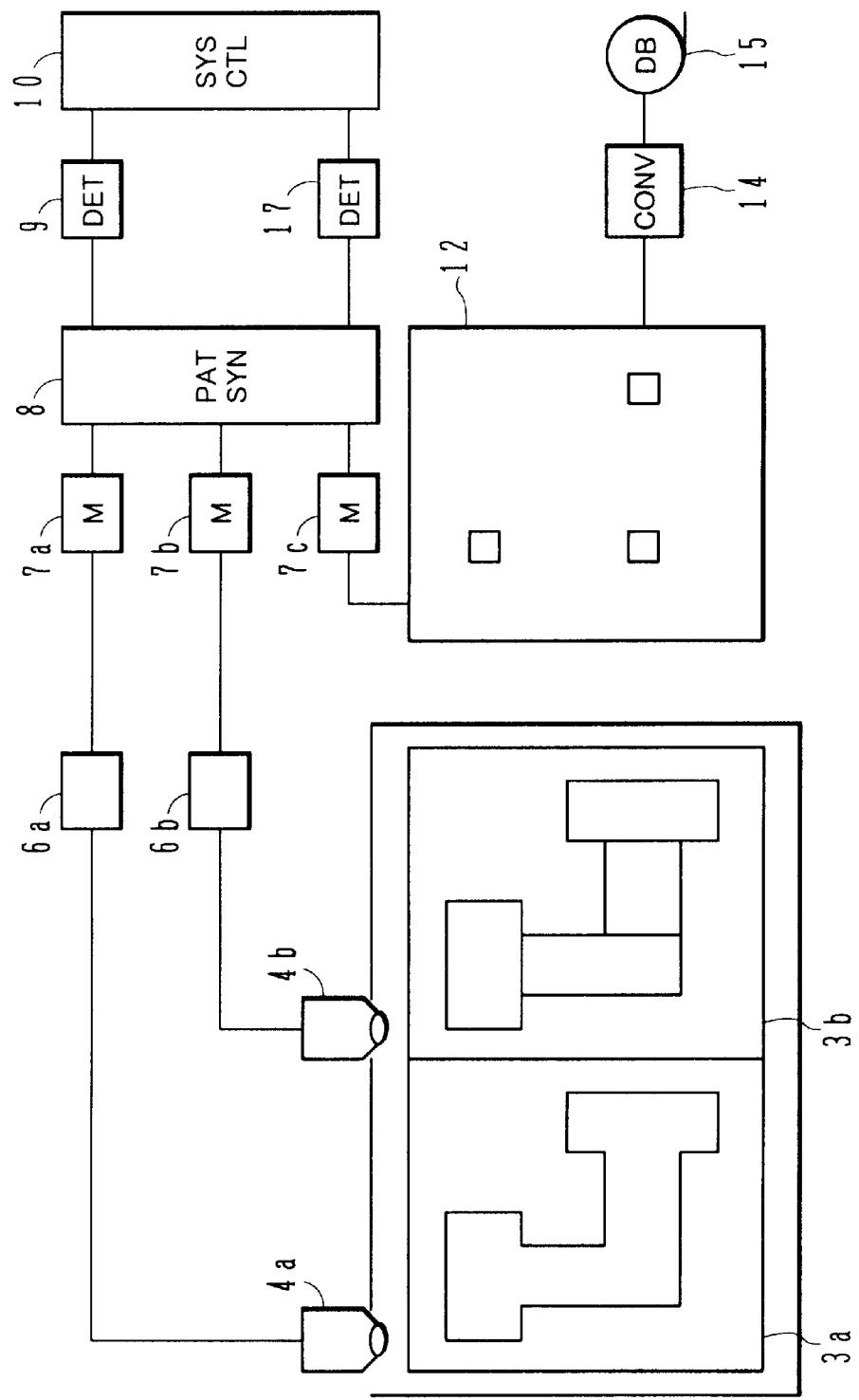
FIG. 5 is a schematic diagram illustrating the operation of the pattern inspection apparatus taking the connection state shown in FIG. 3B.

FIG. 5 shows examples of patterns obtained at the connection state shown in FIG. 3B wherein the selector switch 11 connects the light reception element 6a to the image memory 7a and the image developer 12 to the image memory 7c, with the light reception element 6b being connected to the image memory 7b. The light reception elements 6a and 6b pick up patterns of the same kind and store the image data in the image memories 7a and 7b. The image developer 12 supplies the reference image data at a different layer to the image memory 7c. The pattern synthesizer 8 synthesizes these image data for the comparison inspections of presumably identical patterns and of patterns at different layers. The fine defect detector 9 performs a comparison inspection of presumably identical patterns, and the defect detector 17 performs a comparison inspection of patterns at different layers. These comparison inspection operations are controlled by the system controller 10.

The fine defect detector 9 performs a comparison inspection like a conventional die-to-die or plate-to-plate comparison inspection, relative to presumably identical patterns picked up from the inspection workpieces 3a and 3b. Since presumably identical patterns are compared, this operation can be executed at high speed and with a high defect detection precision.

The defect detector 17 performs a comparison inspection between two patterns selected from the image data of the inspection workpieces 3a and 3b and the image data at a different layer developed by the image developer 12. In this case, the subjects to be inspected are very limited, such as a presence/absence of paired sides and distances between paired sides. Therefore, the inspection can be completed in relatively short time.

FIGS. 6A, 6B, and 6C show examples of patterns with or without defects. FIG. 6A shows a normal pattern, and FIGS. 6B and 6C show patterns with various defects. FIG. 6B shows a pattern having a pin dot F1 which is an isolated miss pattern, a pin hole F2 which is an isolated crevice, a protrusion F3 extending from the normal pattern, a notch F5 retracted from the normal pattern, and a miss size defect F8 with a different size. FIG. 6C shows a pattern having a short defect F4 short cutting the separated area, a crack F6 breaking the continuous area, a position shift defect F7, and a miss size defect F8.

The inspection criteria change with an inspection subject, and can be set by a defect size. For example, defects having a position shift of 0.25 μm or larger and defects having an area or step height of this dimension or higher are detected, and defects smaller than 0.25 μm (or 0.25 μm square) are discarded. Speed of defect inspection can be increased in this manner.

A defect is detected in accordance with "difference of area", "position shift", or the like.

For the design rule check, it is checked for both the same patterns (at the same layer) and the different layers whether there is a pattern having a dimension less than the predetermined minimum line width. If there is such a pattern, it is counted as a defect. For the different layers, it is also checked whether there is an area or gap where superposed two patterns have a dimension less than the predetermined line width (or gap). If there is such an area, it is counted as a defect.

For the design rule check, only the minimum dimension is checked. In most cases, only two directions including the X (right and left) direction and Y (up and down) direction are checked for the design rule check. However, since some patterns have oblique stripe patterns, four directions (or eight directions) such as described with FIG. 4B are checked for whether the line width (gap between lines) is smaller than a predetermined value to count a defect.

A high precision defect detection can be achieved by executing such two types of inspections. A comparison inspection having a high detection sensitivity like a conventional die-to-die or plate-to-plate comparison inspection becomes possible. Furthermore, the same defects, which cannot be detected by a conventional die-to-die or plate-to-plate comparison inspection, can be detected by a limited number of types of comparison inspections to be performed by the defect detector 17.

As above, by using the pattern of an inspection workpiece and a corresponding pattern obtained from a database, a comparison inspection can be executed efficiently and in a short time.

Above, defect inspection of real patterns which are actually formed on a specimen is mainly described. Below, embodiments which can detect mistakes even if there is a mistake on a database are described.

Figure 7A:
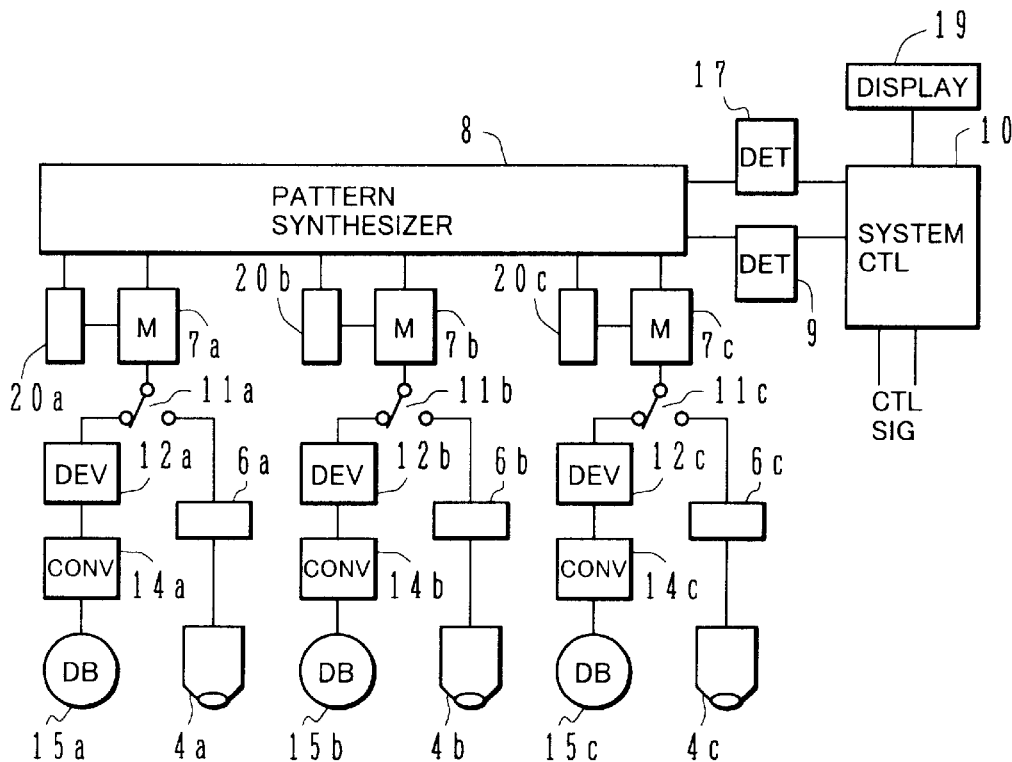
FIGS. 7A and 7B are a block diagram of a defect inspection system and a flow chart illustrated a defect inspection method according to further embodiment of this invention.

FIG. 7A is block diagram schematically showing the structure of a defect detection system according to another embodiment of this invention. Those constituent elements similar to those of FIG. 1 are designated by similar reference numerals, and the descriptions thereof may be omitted. A pattern synthesizer 8 is connected to image memories 7a, 7b, and 7c, similar to the structure of FIG. 1. Each of the image memories 7a, 7b, and 7c is connected to a database detection system and an optical pattern detection system through change over switch 11a, 11b, or 11c.

The database detection system includes a serial circuit of a database 15a, 15b, or 15c, a data converter 14a, 14b, or 14c, and an image developer 12a, 12b, or 12c. The optical pattern detection system includes a serial disposition of an object optical system 4a, 4b, or 4c and a light reception element 6a, 6b, or 6c. Here, the alphabetical letter annexed to a numeral represents which assembly it belongs to, the assemblies being classified by the respective image memories. The assembly will also be called "route".

Registers 20a, 20b, and 20c are connected to the image memories 7a, 7b, and 7c respectively and to the pattern synthesizer circuit 8. A fine defect detector 9 and a defect detector 17 are connected to the pattern synthesizer 8 and the system controller 10, similar to the structure of FIG. 1.

The defect detector 17 includes comparators for detecting superposition of a plurality of patterns at the same position, contour detectors for detecting the continuity of patterns, etc.

A display 19 is controlled by the system controller 10 and displays the result obtained in the defect detector 17, or the fine defect detector 9, etc. and the synthesized patterns obtained in the pattern synthesizer 8.

In this figure, the automatic focussing mechanism, the light source and the XY stage are not shown for the convenience of drawing.

When compared to the structure of FIG. 1, the structure of FIG. 7A has features that each route of the three route a, b, and c, is enabled to detect patterns either optically or from the database, and that each route has a register connected to the image memory. It will be obvious for those skilled in the art that this system can be used to achieve the pattern inspection as described above.

Figure 7B:
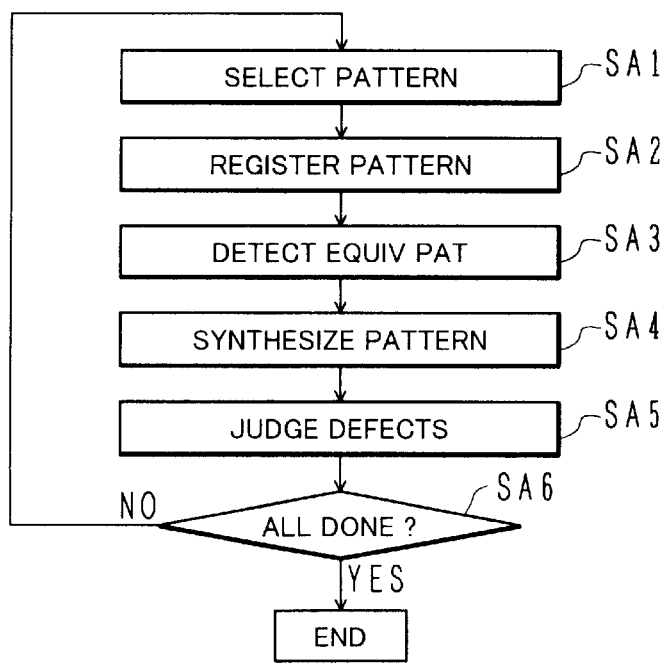

FIG. 7B shows a flow chart illustrating another defect detection method which can be achieved in the pattern detection system shown in FIG. 7A.

In step SA1, an inspector which achieves pattern inspection selects a desired pattern on the display 19, etc. For example, in a wiring pattern picture read out from the database 15a, a configuration of one wide portion representing a contact area is selected.

In step SA2, the selected pattern is registered in a register 20A. At this time, when equivalent patterns obtainable by symmetric operation such as rotation, mirror reflection, etc. should also be included, registration of such symmetric operations may also be done. The selected pattern and the patterns obtainable by symmetric operation are collectively called patterns of equivalent configuration.

In step SA3, patterns of equivalent configuration are extracted or detected from the same image data containing the selected pattern. Here, the area of detection can be optionally limited. Namely, after one pattern from the image date read out from the database 15a is selected and registered, patterns of equivalent configuration are detected from the whole image data or a part of the image data obtained from the database 15a. The detected patterns are stored in the pattern synthesizer 8.

FIGS. 8A to 8E are schematic diagrams for illustrating the steps SA1 to SA3 of FIG. 7B.

Figure 8A:
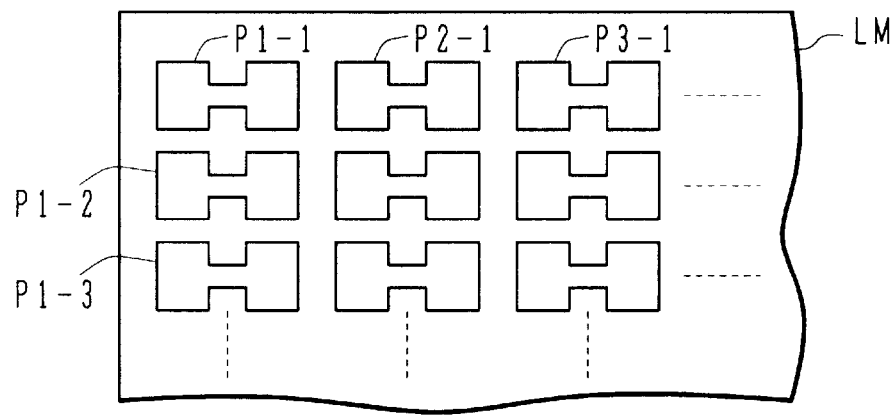
FIGS. 8A to 8E are schematic plan views for illustrating the content of the flow chart of FIG. 7B.

FIG. 8A shows an image data of a metal wiring layer LM as an example of the image data. Wiring patterns P1-1, P1-2, . . . , P2-1, . . . (collectively called P) are disposed as shown in the figure. Each pattern P has wide contact areas at both ends and narrow wiring portion connecting the contact portions.

Figure 8B:

FIG. 8B shows an example of a pattern to be selected and registered at steps SA1 and SA2. Let us assume that a left side contact area Pa in either one pattern P is selected. Here, for designating the connection of the contact portion and the wiring portion, a part of the wiring portion is also selected. Upon such selection, it is clarified that the left side contact portion is selected in the wiring patterns of FIG. 8A.

Figure 8C:
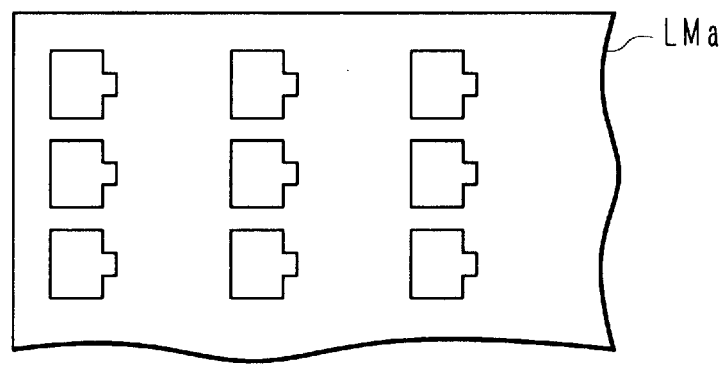

FIG. 8C shows patterns detected in step SA3. Based on the selection and registration as shown in FIG. 8B, patterns having the same configuration as the pattern of FIG. 8B are detected from the patterns of the metal wiring layer LM, to form an image data of detected metal wiring LMa. For each wiring pattern, the portion from the central wiring portion to the right contact portion is not detected.

Figure 8D:
Figure 8E:
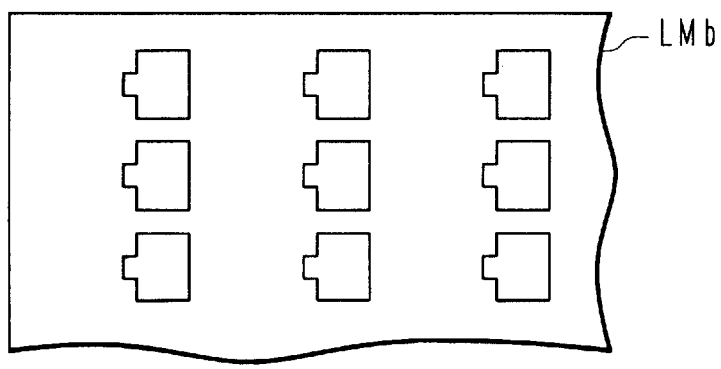

FIGS. 8D and 8E show another example when the pattern to be selected and registered is changed. As shown in FIG. 8D, a pattern Pb formed of a right side contact portion and a continuing part of wiring portion of one metal wiring pattern is selected and registered. The patterns to be detected in step SA3 become detected metal wiring LMb as shown in FIG. 8E. In this case, in each pattern of the metal wiring layer LM, the left side contact portion and the continuing wiring portion are not detected. In this way, by registering a pattern Pa or Pb, patterns of same configuration are selected from the subject image data to produce image data LMa or LMb. When a pattern is registered as shown in FIG. 8B or 8D, if 180° rotation is included, patterns of equivalent configuration obtainable by 180° rotation become also the subject to be detected. Then, an image data obtainable by adding those shown in FIG. 8C and 8D will be obtained. In this way, it becomes possible to extract only the regions which the inspector wishes to inspect defects from a complicated image data, by selecting and registering a specific pattern and extracting patterns of equivalent configuration from the whole or part of the image data.

Returning to FIG. 7B, in step SA4, an associated image data which is the image data on a different layer than that of the extracted pattern and having strong relationship with the extracted pattern is taken out for performing defect inspection on the extracted patterns of equivalent configuration. For example, the image data of the database 15b is taken out through the image memory 7b and loaded in the pattern synthesizer 8. This image data and the extracted group of patterns are synthesized in the image synthesizer 8.

In step SA5, defect discrimination is done in the defect detector 17 using the synthesized image of the group of extracted patterns and the image data of different layer having strong relationship.

Figure 9A:
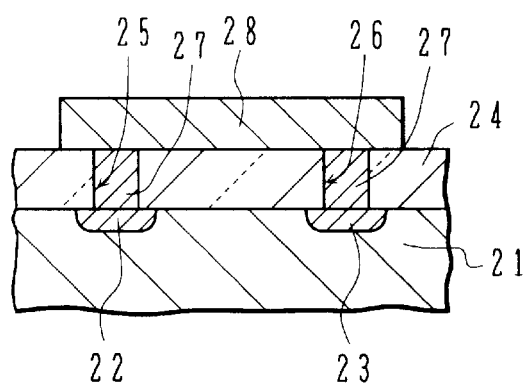
FIGS. 9A to 9E are a schematic cross section of a semiconductor device and schematic plan views of patterns for illustrating an example of defect detection.

FIGS. 9A to 9E illustrate an example of defect detection as described above. FIG. 9A is a cross section showing a structure of a semiconductor device to be manufactured. For example, in a surface of a p-type silicon substrate 21, n-type regions 22 and 23 are formed. The n-type regions 22 and 23 are regarded to constitute a wiring layer. An insulating layer 24 is formed on the surface of the silicon substrate 21. Contact holes 25 and 26 are opened through the insulating layer 24 to expose n-type regions 22 and 23. Conductive plugs 27 are embedded in the contact holes 25 and 26. Then, a wiring pattern 28 is formed thereon to connect the conductive plug 27.

Figure 9B:
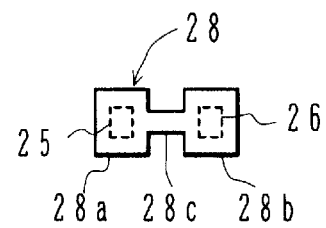

FIG. 9B schematically shows a shape of a wiring pattern 28. The wiring pattern 28 has contact portions 28a and 28b at the two ends, and a wiring portion 28c connecting the two contact portions 28a and 28b. Central areas of the contact portion 28a and 28b are positionally registered or aligned with the contact holes 25 and 26 to be disposed thereunder.

It is assumed that the wiring pattern to be formed is as shown in FIG. 8A.

Figure 9C:
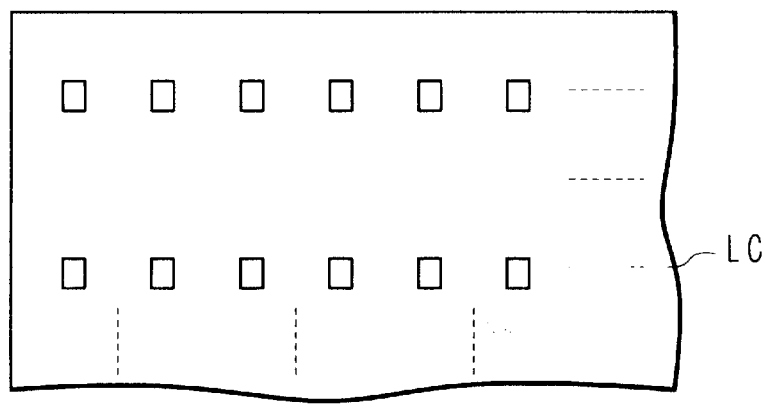

FIG. 9C shows image data of the contact hole layer LC to be connected to the wiring layer of FIG. 8A. Here, in the region where three rows of wiring patterns are disposed in FIG. 8A, only two rows of contact holes are formed in the layer LC of FIG. 9C. Namely, contact patterns for an intermediate row of the wiring layer are dropped by a mistake of a designer.

Figure 9D:
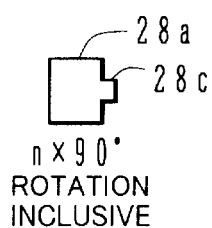

FIG. 9D shows patterns to be detected in the wiring layer for inspecting the alignment or superposition relationship between the wiring layer and the contact hole layer. It is assumed here that an inspector takes out one of the wiring patterns as shown in FIG. 8A, selects the left side contact portion 28a and a continuing part of the wiring portion 28c of the taken out pattern, and registers the condition of allowing n×90° rotation. In the wiring patterns as shown in FIG. 9B, a pair of contact portions are in the relationship of 180° rotation. Therefore, by the condition of allowing n×90° rotation, all the contact portions are detected. Namely, contact portions as shown in FIG. 8C and contact portions as shown in FIG. 8E are collectively detected.

Figure 9E:
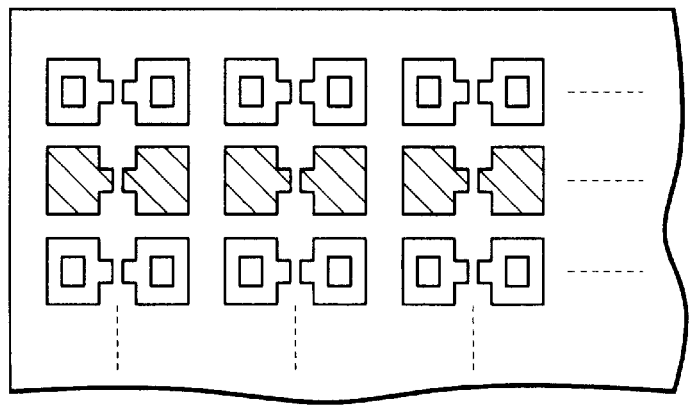

FIG. 9E shows all the contact portions thus detected.

Further, the image data of contact holes as shown in FIG. 9C is selected and synthesized with the wiring patterns previously detected. The result is shown in FIG. 9E.

Regarding the wiring patterns of the first row and the third row, contact holes are superposedly disposed on the respective contact portions. With regard to the wiring patterns of the second row, only the wiring patterns exist, but there exist no contact holes which should be associated.

For example, the wiring patterns are displayed by a first color, e.g. blue, and contact holes are displayed by a second color, e.g. yellow on a display. Then, superposition is displayed in green.

It is judged that the regions are normal where the detected pattern (wiring pattern) from the first image and an associated pattern (contact hole pattern) of the second image are superposed. Those areas where only one of the two kinds of patterns exists are judged as defects, and may be displayed by a third color, for example red on the display 19. In the case where the respective patterns are represented by dots, the superposition of two patterns can be discriminated by the fact that dots of the two patterns exist at the same position.

The above-described steps, except the selection of a pattern in step SA1 and selection of the image data on a different layer in step SA4, can be all carried out automatically.

FIGS. 10A to 10K show another example of defect detection.

Figure 10A:
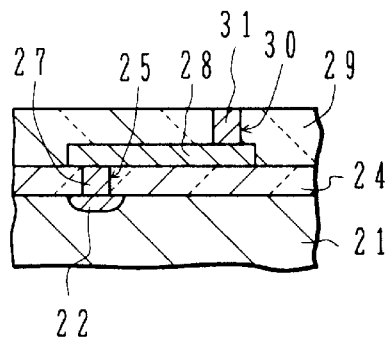

FIG. 10A is a cross section showing a structure of a semiconductor device to be manufactured. In a surface of a p-type silicon substrate 21, an n-type region 22 is formed. An insulating layer 24 is formed to cover the p-type silicon substrate 21. A contact hole 25 is formed to expose the n-type region 22. The contact hole 25 is embedded with an electrically conductive plug 27. A wiring pattern 28 is formed on the surface of the insulating layer 24 so that one end of the pattern 28 is connected to the conductive plug 27. Another insulating layer 29 is formed to cover the wiring pattern 28. Another contact hole 30 is formed to expose the other end of the wiring pattern 28. Another electrically conductive plug 31 is formed to embed the contact hole 30.

Although the cases where wiring layers or conductive layers are connected through electrically conductive plugs, an upper wiring layer may be formed to embed a contact hole or holes to form connection between wiring layers.

Figure 10B:
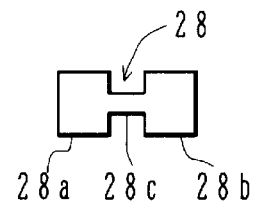

FIG. 10B shows the plan shape of the wiring pattern 28. Contact portions 28a and 28b at the both ends are connected through intermediate narrow wiring portion 28c.

Figure 10C:
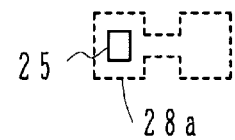

FIG. 10C shows a contact hole pattern to be disposed under the wiring layer 28. The contact hole 25 is formed in alignment with the left side contact portion 28a of the wiring pattern 28.

Figure 10D:
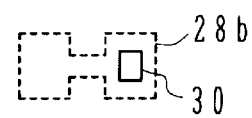

FIG. 10D shows a contact hole pattern above the wiring layer 28. The contact hole 30 is formed in alignment with the right side contact portion 28b of the wiring pattern 28. If the defect detection as described with reference to FIGS. 9A to 9E is done on this structure, many pseudo defects can be generated. Namely, two layers of contact hole patterns are associated with one wiring layer. Therefore, two contact portions of a wiring pattern should be discriminated and selectively detected.

Figure 10E:
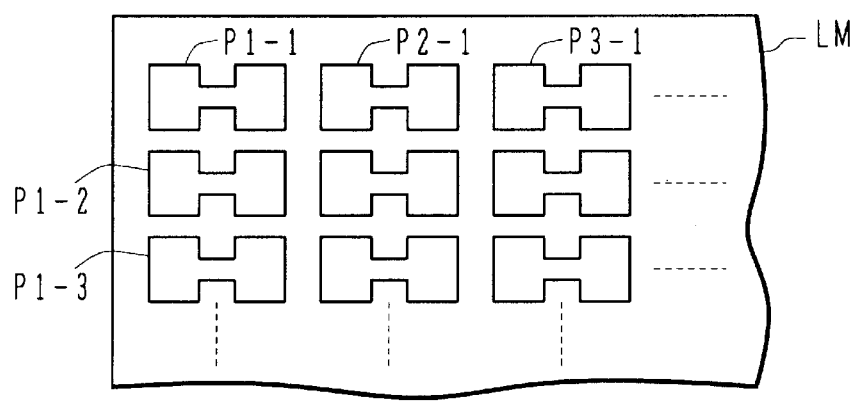

FIG. 10E shows pattern configuration of a metal wiring layer LM. In the region shown in the figure, wiring patterns of three rows and three columns are disposed.

Figure 10F:
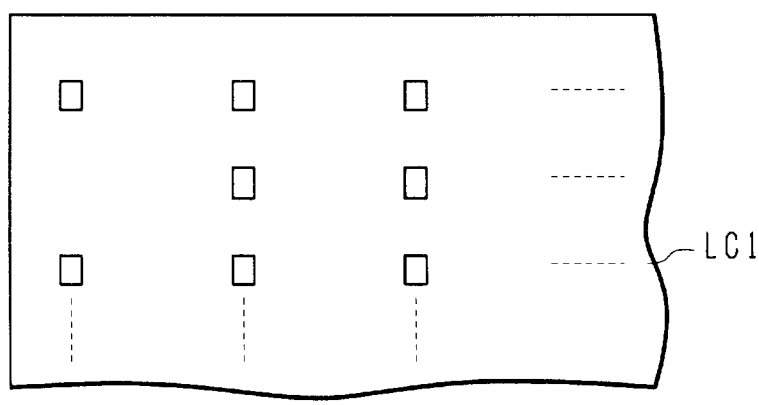

FIG. 10F shows contact hole pattern layer LC1 under the wiring layer. In the region shown in the figure, contact holes of three rows and three columns are disposed. Here, however, a contact hole pattern at the second row and first column is missing.

Figure 10G:
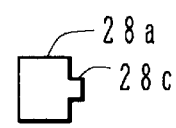

As shown in FIG. 10G, the left side contact portion 28a and a continuing portion of the wiring portion 28c of an wiring pattern is selected and registered for detecting the associated relationship with the lower contact hole pattern layer LC1.

Contact portions of the same configuration as the contact portion shown in FIG. 10G are extracted, and synthesized with the contact hole patterns shown in FIG. 10F.

FIG. 10H shows an obtained superposed pattern SP1. Each of the left side contact portions and a lower contact hole pattern are superposedly disposed. Here, for the contact portion of the second row and first column, there exists no associated contact hole pattern. Thus, the lack of a contact hole pattern is detected and discriminated as defect D1. The defect D1 is displayed on the display as described before, for example in red.

The relationship of superposition between the lower contact hole pattern and the wiring pattern can be inspected by the above-described processes. The relationship of superposition between the upper contact hole pattern and the wiring pattern is not inspected yet.

Returning to FIG. 7B, after one defect detection is finished, it is discriminated whether all the defects to be detected have been detected or not in step SA6. If all the detects have not been detected yet, the flow returns to step SA1 according to the arrow NO. Then, next pattern is selected and registered, and an image data on a different layer and having strong relationship with the selected pattern is selected. Similar defect detection is carried out as described above. When all the defects have been detected in step SA6, the defect detecting process is finished according to the arrow YES.

In the structure of FIG. 10A, the relationship of superposition between the wiring pattern 28 and the upper contact hole 30 is inspected as follows.

FIG. 10I shows upper contact hole pattern layer LC2. In the region shown in the figure, a contact hole pattern at the first row and first column is missing.

As shown in FIG. 10J, the right side contact portion 28b and a continuing portion of the wiring portion 28c of a wiring pattern is selected and registered, for detecting the relationship or correspondence with the upper contact hole patterns.

When the pattern of FIG. 10J is registered and the contact hole pattern layer of FIG. 10I is selected as an image data on a different layer having a strong relationship, a result as shown in FIG. 10K is obtained. Namely, right side contact portions of the respective wiring patterns and upper contact hole patterns are synthesized. Those regions where only one of the two kinds of patterns of different layers exists, are discriminated as defects D2, and are displayed on the display, for example in red.

FIGS. 11A to 11C show a case where unnecessary patterns are formed by mistake. FIG. 11A shows contact hole pattern layer LC2 similar to that of FIG. 10I. In the configuration shown in the figure, contact hole patterns of one column at the leftmost position should not belong to this contact hole layer, and should belong to the other contact hole layer. These contact holes at the leftmost column are formed by mistake.

FIG. 11B shows a pattern to be selected and registered, similar to FIG. 10J. Namely, in the structure as shown in FIGS. 10B to 10D, the right side contact portion 28b and a continuing portion of the wiring portion 28c' which should be connected to the upper contact hole, is registered.

FIG. 11C shows a synthesized image SP2 which is synthesized from the group of patterns of equivalent configuration extracted from the wiring layer as shown in FIG. 10E and contact hole patterns as shown in FIG. 11A. For the leftmost column of contact hole patterns, there exist no corresponding contact portions of the wiring layer. These contact hole patterns are discriminated as defects D3, and displayed on the display in red, etc.

Description has been made on the case where two kinds of patterns which should be superposed are detected, and the regions where only one of the two kinds of patterns exists are detected as defects. It is also possible to detect two kinds of patterns which should not be superposed, and to discriminate those regions where the two kinds of patterns are superposed as defects.

In the defect detection as described above, description has been made on the case where a specific pattern is selected and where after a specific pattern is selected and registered, patterns of equivalent configuration are extracted from the whole image data of one layer. If the whole region is wide and the region to be subjected to defect detection is limited, a desired region in the whole area can be designated and patterns of equivalent configuration can be detected in the designated limited region.

Similarly, for the image data on a different layer, a portion thereof may be extracted. As the method of extracting a portion, any one of the following methods can be employed: a method of designating a region by coordinates; a method of designating part of a plurality of sublayers constituting one layer in case the database is separated in several files; in case the image data is annexed with a discriminator which represent a characteristic of the data, a method of designating data by the discriminator, etc. Similar selection can be made for the first image data to be subjected to pattern selection and registration.

As the image data on a different layer, which is displayed superposedly after patterns of equivalent configuration are detected, an additional condition can be posed that only those patterns which are superposed on the detected group of patterns of equivalent configuration are displayed. In this case, superposition may cover not only superposition on the same position but also dispositions in a neighborhood.

In the structure of FIG. 7A, three routes of image data detection are shown. By such a structure, an image data of one layer such as wiring layer and two image data to be disposed above and below said one layer can be concurrently inspected. It is possible to carry out the inspection of the corresponding relationship between the wiring layer and the lower contact hole layer and inspection of a corresponding relationship between the wiring layer and the upper contact hole layer, in parallel.

Figure 12:
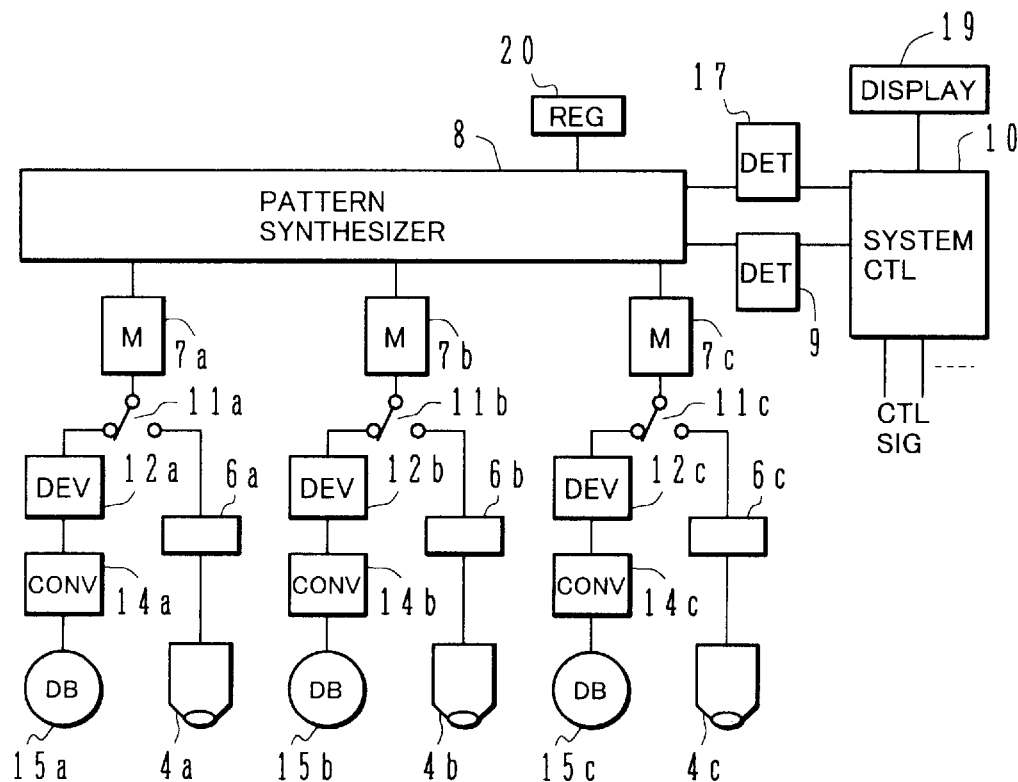
FIG. 12 is a block diagram of a defect inspection system according to another embodiment of this invention.

FIG. 12 shows an alternative configuration of the defect inspection system. In place of using three registers, only one register 20 connected to the pattern synthesizer 8 is employed to be commonly used for the three image memories 7a, 7b and 7c through the pattern synthesizer 8. Defect inspection can be carried out in the similar way as described above.

Figure 13:
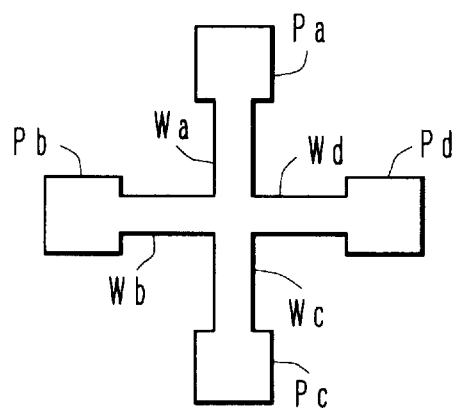
FIG. 13 is a schematic plan view of another example of a wiring pattern.

FIG. 13 shows another example of a wiring pattern. Four contact portions Pa, Pb, Pc, and Pd are connected by wiring portions Wa, Wb, Wc, and Wd. The four contact portions are in the relationship of n×90° rotation. If the contact portion Pa is selected with a condition of allowing +90° rotation, contact portions corresponding to the contact portions Pa and Pb will be detected. Various other conditions for detecting particular equivalent configurations would be obvious. It will be apparent for those skilled in the art that the above described defect inspection can be applied to various pattern shapes.

Further, if the number of image detection routes is increased, it is possible to continuously or concurrently perform defect detection of four or more layers.

Description has been made on example where defects of database of image data are detected, it will be obvious that real pattern or patterns actually formed on a specimen are read by objective optical system 4 and the light reception element 6 and similar defect detection can be performed. Namely in the case where image data of three layers having a mutually strong relationship are subjected to defect detection, the image data of three subject layers can be all database layers, all real pattern layers, one real pattern layer and two database layers, two real pattern layers and one database layer.

The present invention has been described in connection with the preferred embodiments. The invention is not limited only to the above embodiments. It is apparent to those skilled in the art that various modifications, improvements, combinations, and the like can be made.

What is claimed is:

1. A pattern inspection method comprising the steps of: obtaining first image data by optically picking up a first pattern actually formed;
   aligning a position of the first image data with second image data of a second pattern at a different layer from that of the first image data, the second pattern being different than the first pattern; and
   performing a first pattern inspection using the first and second image data, including a distance between paired lines in different layers, to detect a pattern defect.

2. A pattern inspection method according to claim 1, wherein said step of performing a first pattern inspection comprises the step of checking for a presence of paired sides of said first and second patterns.

3. A pattern inspection method according to claim 2, wherein said step of performing a first pattern inspection further comprises the step of checking a distance between paired sides of said first and second patterns.

4. A pattern inspection method according to claim 1, further comprising the steps of:
   obtaining third image data by optically picking up a third pattern actually formed; and
   performing a second pattern inspection using the first and third image data, in parallel with the first pattern inspection.

5. A pattern inspection method according to claim 1, wherein the second image data is generated by using design data.

6. A pattern inspection method according to claim 1, wherein the second image data is generated by using image data optically picked up.

7. A defect detecting apparatus comprising:
   a first optical system to focus an image of a workpiece having a first pattern on an image pickup surface;
   pickup means disposed on the image pickup surface of said first optical system for supplying image data of the first pattern;
   image data supplying means for supplying image data of a second pattern at a layer different from that of the first pattern, the second pattern being different than the first pattern; and
   a defect detector circuit to compare the image data of the first pattern supplied from the pickup means with the image data of the second pattern, including a distance between paired lines in different layers, supplied from the image data supplying means to detect a pattern defect.

8. A defect detecting apparatus according to claim 7, wherein said image data supplying means includes a second optical system and second pickup means equivalent to said optical system and said pickup means, or means for developing image data read from a database.

9. A defect detecting apparatus according to claim 7, wherein said defect detector circuit can check a presence of paired sides.

10. A defect detecting apparatus according to claim 9, wherein said defect detector circuit can detect a distance between paired sides of said first and second patterns.

11. A pattern inspection method comprising the steps of:
   a) providing first image data on a first layer;
   b) registering a first pattern which is a part of said first image data;
   c) detecting a first group of patterns of equivalent configuration to said first pattern from said first image data;
   d) providing a first associated group of patterns on a second layer different from that of said first image data which include second image data, the second image data being different than the first image data; and
   e) comparing said first group of patterns and said first associated group of patterns to detect a pattern defect.

12. A pattern inspection method according to claim 11, wherein said step a) or d) includes a sub-step of retrieving a part of the first or second image data.

13. A pattern inspection method according to claim 12, wherein said sub-step includes selecting one of a plurality of sub-layers which constitute said first or second image data.

14. A pattern inspection method according to claim 12, wherein said sub-step includes designating a part of an area of said first or second image data and detecting patterns in said designated part of the area.

15. A pattern inspection method according to claim 12, wherein said step d) includes the step of detecting patterns positionally registered with said first group of patterns, from patterns constituting said second image data, as said first associated group of patterns.

16. A pattern inspection method according to claim 11, wherein said step e) includes a sub-step of discriminating relationship of superposition between said first group of patterns and said first associated group of patterns.

17. A pattern inspection method according to claim 16, wherein said step e) further includes a sub-step of discriminating a defect when any pattern of one of said first group and said first associated group does not superpose on a pattern of the other of said first group and said first associated group.

18. A pattern inspection method according to claim 16, wherein said step e) further includes a sub-step of discriminating a defect when any pattern of one of said first group and said first associated group superposes on a pattern of the other of said first group and said first associated group.

19. A pattern inspection method according to claim 11, further comprising the steps of:
   f) providing a second associated group of patterns different than said first group of patterns and said first associated group of patterns which includes third image data on a;
   g) registering a second pattern different than said first pattern which is a second part of said first image data;

h) detecting patterns of equivalent configuration to said second pattern from said first image data, as second group of patterns; and i) comparing said second group of patterns and said second associated group of patterns.

20. A pattern inspection method according to claim 19, wherein said step f) includes a sub-step of:

f-1) retrieving a part from image data of a fourth layer.

21. A pattern inspection method according to claim 20, wherein said sub-step f-1) includes the step of selecting one of a plurality of sub-layers which constitute said image data of said fourth layer.

22. A pattern inspection method according to claim 20, wherein said sub-step f-1) includes designating a part of an area of said image data of said fourth layer and detecting patterns in said designated part of the area.

23. A pattern inspection method according to claim 20, wherein said sub-step f-1) includes the step of detecting patterns positionally registered with said second group of patterns, from patterns constituting said image data of said fourth layer, as said second associated group of patterns.

24. A pattern inspection method according to claim 20, wherein said step I) includes a sub-step of discriminating relationship of superposition between said second group of patterns and said second associated group of patterns.

25. A pattern inspection method according to claim 24, wherein said step I) further includes a sub-step of discriminating a defect when any pattern of one of said second group and said second associated group does not superpose on a pattern of the other of said second group and said second associated group.

26. A pattern inspection method according to claim 24, wherein said step i) further includes a sub-step of discriminating a defect when any pattern of one of said second group and said second associated group superposes on a pattern of the other of said second group and said second associated group.

27. A pattern inspection system comprising:

a) means for providing first image data on a first layer;

b) a register connected to said means to provide first image data and register a first pattern which is a part of said first image data;

c) a detector connected to said means for providing first image data and said register, and to detect a first group of patterns of equivalent configuration to said first pattern from said first image data;

d) means for providing second image data including a first associated group of patterns on a second layer; and e) a comparator connected to said detector and said means for providing second image data, to compare said first group of patterns and said first associated group of patterns to detect a pattern defect.

28. A pattern inspection system according to claim 27, further comprising: f) means for providing third image data including a second associated group of patterns, wherein said comparator is also connected to said means f) and can compare said first group of patterns and said second associated group of patterns.

* * * * *

UNITED STATES PATENT AND TRADEMARK OFFICE
CERTIFICATE OF CORRECTION

PATENT NO.:    6,064,484
DATED     :    May 16, 2000
INVENTOR(S):   Ken-ichi KOBAYASHI et al.

It is certified that error appears in the above-identified patent and that said Letters Patent is hereby corrected as shown below:

Col. 16,    line 65, after "on a" insert --third layer--.

Signed and Sealed this

Twenty-seventh Day of March, 2001

Attest:

NICHOLAS P. GODICI

Attesting Officer

Acting Director of the United States Patent and Trademark Office